United States Patent [19]
Björk et al.

[11] Patent Number: 5,661,183
[45] Date of Patent: Aug. 26, 1997

[54] 3-HYDROXY ANTHANILIC ACID DERIVATIVES

[75] Inventors: Susanna Karin Maria Björk, Södertälje; Birgitta Kristina Gotthammar, Stockholm; Mats Torbjörn Linderberg, Södertälje; Johan Per Luthman, Gnesta; Kerstin Margareta Irma Persson, Nykvarn, all of Sweden; Robert Schwarcz, Baltimore, Md.

[73] Assignees: The University of Maryland, Baltimore, Md.; Astra Aktiebolag, Sodertalje, Sweden

[21] Appl. No.: 433,339

[22] PCT Filed: Feb. 22, 1994

[86] PCT No.: PCT/SE94/00152

§ 371 Date: May 4, 1995

§ 102(e) Date: May 4, 1995

[87] PCT Pub. No.: WO94/19315

PCT Pub. Date: Sep. 1, 1994

[30] Foreign Application Priority Data

Feb. 22, 1993 [SE] Sweden ................... 9300657

[51] Int. Cl.$^6$ ................ A61K 31/195; C07C 229/00
[52] U.S. Cl. ................ 514/567; 558/411; 558/412; 562/453
[58] Field of Search ................ 562/453; 514/567; 558/411, 412

[56] References Cited

PUBLICATIONS

Prinz et al., "A Novel Synthetic Route To Oximindace T–2–Anisidides And Their Conversion To 3–Hydroxyanthranilic Acids Via 7–Methoxyisatins," J. Chem. Research (M), pp. 1346–1354 (1978).

Heyes et al., "4–Chloro–3–Hydroxy Anthranilate Inhibits Brain 3–Hydroxy Anthranilate Oxidase," Neurochem. Int., vol. 13, No. 3, pp. 405–408 (1988).

Parli et al., "Metabolism of 6–Chlorotryptophan to 4–Chloro–3–hydroxyanthranilic Acid: A Potent Inhibitor of 3–Hydroxyanthranilic Acid Oxidase," Archives of Biochemistry and Bio–physics, vol. 203, No. 1, pp. 161–166 (1980).

Prinz et al., Chemical Abstracts No. 89:197117K, vol. 89, p. 590 (1978).

Todd et al., "Preparation of 4–Halo–3–Hydroxyanthranilates and Demonstration of Their Inhibition of 3–Hydroxyanthranilate Oxygenase Activity in Rat and Human Brain Tissue," Preparative Biochemistry, vol. 19, No. 2, pp. 155–165 (1989).

*Primary Examiner*—Joseph Conrad
*Attorney, Agent, or Firm*—White & Case

[57] ABSTRACT

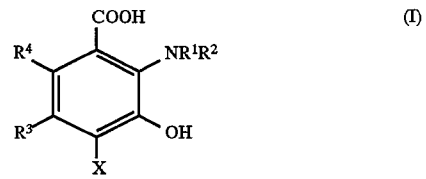

The present invention relates to novel derivatives of 3-hydroxyanthranilic acid, 3-HANA of general formula (I), wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and (a), wherein $R_7$=H or alkyl; or a pharmaceutically acceptable salt thereof, methods and intermediates for their preparation, novel pharmaceutical compositions and the use thereof for inhibiting the enzyme 3-hydroxyanthranilate oxygenase, 3-HAO, responsible for the production of the endogenous neurotoxin quinolinic acid, QUIN.

7 Claims, No Drawings

3-HYDROXY ANTHANILIC ACID DERIVATIVES

FIELD OF INVENTION

The present invention relates to novel derivatives of 3-hydroxyanthranilic acid, 3-HANA, methods and intermediates for their preparation, novel pharmaceutical compositions and the use thereof for inhibiting the enzyme 3-hydroxy-anthranilate oxygenase, 3-HAO, responsible for the production of the endogenous neurotoxin quinolinic acid, QUIN.

BACKGROUND OF THE INVENTION

3-HAO is the enzyme in the catabolic pathway of tryptophan responsible for the conversion of 3-hydroxyanthranilic acid into quinolinic acid. Both QUIN and its biosynthetic enzyme 3-HAO have been identified in rodent as well as in human brain tissue. QUIN is an excitatory amino acid acting through the N-methyl-D-aspartate (NMDA) receptor and has recently gained attention for its putative role as an endogenuos excitotoxin involved in neurodegenerative disorders such as Huntington's disease, stroke/cerebral ischemia, hypoxia, Alzheimer's disease and the Aids dementia complex as well as epilepsi. Inhibitors of 3-HAO activity are of obvious therapeutic interest in diseases which can be traced to an overabundance of quinolinic acid.

PRIOR ART

4-Halogenated substrate analogs have been described as inhibitors of 3-HAO activity. In 1980 it was shown by Parli C J, Krieter P, Schmedt B, in "Metabolism of 6-chlorotryptophan to 4-chloroanthranilic acid: A potent inhibitor of 3-hydroxyanthranilic acid oxidase", Arch Biochem and Biophys 203, pp 161–166, 1980, that 4-chloro-3-hydroxyanthranilic acid, a metabolite of 6-chlorotryptophan, is a potent inhibitor of 3-HAO in rat and pig liver and kidney. Later it was verified by Heyes M P, Hutto B, Markey S P, in "4-Chloro-3-hydroxyanthranilate inhibits brain 3-hydroxy-anthranilate oxidase", Neurochem Int 13, pp 405–408, 1988, that 4-chloro-3-hydroxyanthranilic acid also is an inhibitor of rat brain 3-HAO. In 1989 Todd W P, Carpenter B K and Schwarcz R, in "Preparation of 4-halo-3-hydroxyanthranilates and demonstration of their inhibition of 3-hydroxyanthranilate oxygenase activity in rat and human brain tissue." Prep Biochem 19, pp 155–165, 1989, showed that 4-fluoro-, 4-chloro- and 4-bromo-3-hydroxyanthranilic acid had very similar blocking potencies of 3-HAO in rat as well as in human brain.

BRIEF DESCRIPTION OF INVENTION

The present invention relates to compounds able to inhibit the enzyme 3-HAO with $IC_{50}$ values similar to and in addition a stability superior to compounds according to the prior art.

The present invention, thus is related to a compound of the general formula I

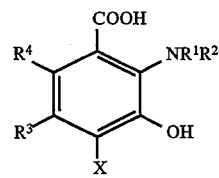

wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl; or a pharmaceutically acceptable salt thereof.

Another object of the invention is a process for the preparation of the compound of formula I by
A) in the case where $R^1$ and $R^2$=H; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl
reducing a compound of formula II

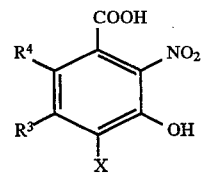

wherein X, $R^3$ and $R^4$ are as defined in A) above,
B) in the case where $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl deprotecting a compound of formula III

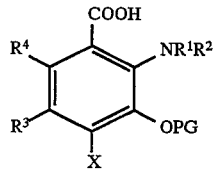

wherein $R^1$, $R^2$, X, $R^3$ and $R^4$ are as defined in B) above and PG is a protecting group such as alkyl, benzyl (Bn), 2-(trimethylsilyl)ethoxymethyl (SEM), methoxymethyl (MOM) or 2-methoxyethoxymethyl (MEM), C) in the case where $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and

wherein $R_7$=H or alkyl deesterifying a compound of formula IV

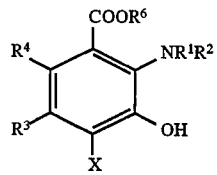

wherein $R^1$, $R^2$, X, $R^3$ and $R^4$ are as defined in C) above and $R^6$ is selected from alkyl, Bn, SEM, MEM, MOM and 2,2,2-trichloroethyl, D) in the case where $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and

wherein $R_7$=H or alkyl deesterifying and deprotecting a compound of formula V

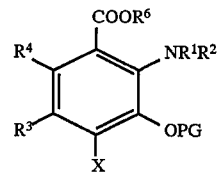

wherein $R^1$, $R^2$, X, $R^3$ and $R^4$ are as defined in D) above and $R^6$ and PG are selected from alkyl, Bn, SEM, MEM and MOM, E) in the case where $R^1$=alkyl, $R^2$=H or alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and

wherein $R_7$=H or alkyl alkylating a compound of formula VI

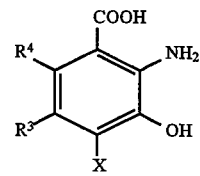

wherein X, $R^3$ and $R^4$ are as defined in E) above.

F) in the case where $R^1$ and $R^2$ are the same or different and selected from H and alkyl; X is selected from alkylthio, halogen and cyano; $R^3$=chloro, bromo or iodo; $R^4$=alkoxy, alkyl, alkylthio, cyano, fluoroalkyl, halogen, $RSO_2$ or RCO wherein R=$C_1$–$C_5$ alkyl halogenating a compound of formula VII

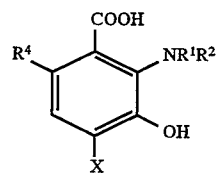

wherein $R^1$, $R^2$, X and $R^4$ are as defined in F) above.

G) in the case where $R^1$ and $R^2$ are the same or different and selected from H and alkyl; X is selected from alkylthio, halogen and cyano; $R^3$=alkoxy, alkyl, alkylthio, cyano, fluoroalkyl, halogen, $RSO_2$ or RCO wherein R=$C_1$–$C_5$ alkyl and $R^4$=chloro, bromo or iodo halogenation a compound of formula VIII

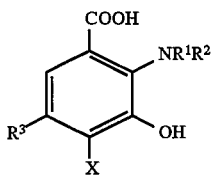

wherein $R^1$, $R^2$, X and $R^3$ are as defined in G) above, or

H) in the case where $R^1$ and $R^2$ are the same or different and selected from H and alkyl; X is selected from chloro, bromo and iodo; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl
halogenating a compound of formula IX

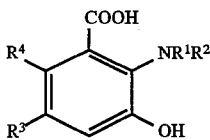

wherein $R^1$, $R^2$, $R^3$ and $R^4$ are as defined in H) above.

The present invention is also related to a pharmaceutical formulation containing a compound of formula I as active ingredient and a pharmaceutically acceptable carrier, the use of said compound for the manufacture of a medicament for the prevention or treatment of neurodegeneration.

Further objects of the invention are synthesis intermediates for the preparation of the compound of formula I, namely a compound of the general formula II

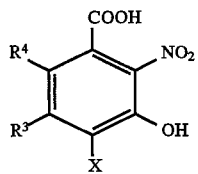

wherein X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl;

a compound of the general formula III

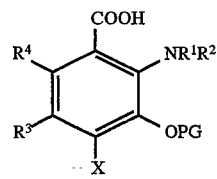

wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl and PG is a protecting group, such as alkyl, benzyl (Bn), 2-(trimethylsilyl)ethoxymethyl (SEM), methoxymethyl (MOM) or 2-methoxyethoxymethyl (MEM);

a compound of the general formula IV

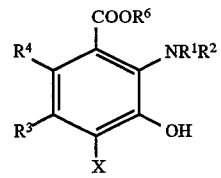

wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl and $R^6$ is selected from alkyl, Bn, SEM, MEM, MOM and 2,2,2-trichloroethyl;

a compound of the general formula V

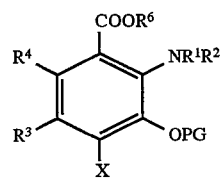

wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl and N=N; $R^6$ and PG are selected from alkyl, Bn, SEM, MEM and MOM;

a compound of the general formula VI

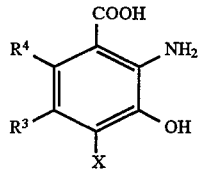

wherein X is selected from alkylthio, arylthio, aryloxy, halogen and cyano; $R^3$, $R^4$ are the same or different and selected from, halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl;

a compound of the general formula VII

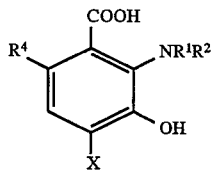

wherein $R^1$ and $R^2$ are the same or different and selected from H and alkyl; X is selected from alkylthio, halogen and cyano; $R^4$ is selected from $RSO_2$ and RCO wherein R=$C_1$-$C_5$ alkyl;

a compound of the general formula VIII

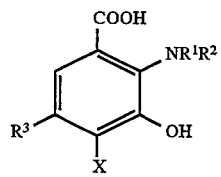

wherein $R^1$ and $R^2$ are the same or different and selected from H and alkyl; X is selected from alkylthio, halogen and cyano; $R^3$ is selected from $RSO_2$ and RCO wherein R=$C_1$-$C_5$ alkyl;
and a compound of the general formula IX

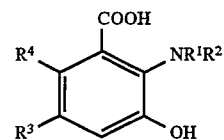

wherein $R^1$ and $R^2$ are the same or different and selected from H and alkyl; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl and fluoroalkyl; or $R^3$ and $R^4$ together form a saturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl.

DETAILED DESCRIPTION OF THE INVENTION

The following definitions shall apply throughout the specification and the appended claims.

Unless otherwise stated or indicated, the term "alkyl" denotes a straight or branched lower alkyl group, preferably a $C_1$-$C_6$ alkyl. Examples of said lower alkyl include methyl, ethyl, n-propyl, iso-propyl, n-butyl, iso-butyl, sec-butyl, t-butyl and straight- and branched-chain pentyl and hexyl.

Unless otherwise stated or indicated, the term "aryl" denotes a phenyl, furyl or thienyl group in which the ring is optionally further substituted by lower alkyl, lower alkoxy or halogen.

Unless otherwise stated or indicated, the term "alkylthio" denotes a straight or branched lower alkylthio preferably a $C_1$-$C_6$ alkylthio. Examples of said lower alkylthio include methylthio, ethylthio, n-propylthio, iso-propylthio, n-butylthio, iso-butylthio, sec-butylthio, t-butylthio and straight- and branched-chain pentylthio and hexylthio.

Unless otherwise stated or indicated, the term "arylthio" denotes a phenylthio group in which the phenyl ring is optionally further substituted by lower alkyl, lower alkoxy or halogen.

Unless otherwise stated or indicated, the term "aryloxy" denotes a phenoxy group in which the phenyl ring is optionally further substituted by lower alkyl, lower alkoxy or halogen.

Unless otherwise stated or indicated, the term "halogen" shall mean fluorine, chlorine, bromine or iodine.

The best mode of carrying out the invention known at present is to use 4,6-dichloro-5-methylanthranilic acid.

The compounds according to the present invention may be used in connection with prevention or treatment of neurodegeneration, especially in connection with conditions such as stroke, cerebral ischaemia, hypoxia, epilepsy and in neurodegenerative diseases such as Alzheimer's disease, multi-infarct dementia, Huntington's disease and the AIDS dementia complex.

Below the methods for the preparation of the compound of formula I will be described in detail.

METHODS OF PREPARATION
Compounds of formula I

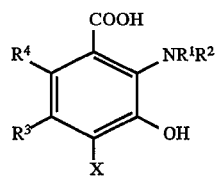

wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and $Z-R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z; are as defined for Z above and V is selected from $C_1$–$C_3$ alkylene or alkenylene, —N=, —N=N— and

wherein $R_7$=H or alkyl; may be prepared by one of the following methods.

Method A Compounds of formula I wherein $R^1$ and $R^2$=H; X is selected from alkylthio, arylthio, aryloxy, halogen and cyano; $R^3$, $R^4$ are the same or different and selected from halogen, methyl, fluoroalkyl, cyano and $Z-R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and

wherein $R_7$=H or alkyl; may be prepared from compounds of formula II

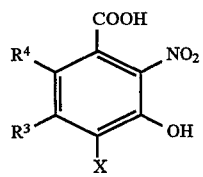

wherein X, $R^3$ and $R^4$ are as defined in formula I in method A, for example by reduction with $H_2$ and a catalyst such as Pd/C, Raney nickel or $PtS_2$ at atmospheric or elevated pressure in a suitable solvent such as EtOH or EtOAc. The reduction can also be accomplished by reaction with $SnCl_2$, $NH_2NH_2\cdot H_2O$ or $Na_2S_2O_5$ in a suitable solvent such as EtOH.

Method B Compounds of the general formula I wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and $Z-R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and

wherein $R_7$=H or alkyl; may be prepared from compounds of formula III

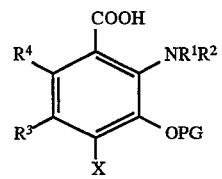

wherein $R^1$, $R^2$, X, $R^3$ and $R^4$ are as defined in formula I in method B and PG is selected from alkyl, Bn, SEM, MEM and MOM, by deprotection with for example a Lewis acid such as $BBr_3$ or trimethylsilyl iodide or with alkyl- or arylSNa or alkyl- or arylSLi followed by adjustment of the pH to obtain the 3-hydroxyanthranilic acid derivative. In the case where PG=SEM, deprotection may be performed using tetrabutylammonium fluoride (TBAF) or CsF in a suitable solvent such as N,N-dimethylpropylenurea (DMPU) or N,N-dimethylformamide (DMF) at elevated temperature. A benzyl group may be removed by hydrogenolysis using for example $H_2$ and Pd/C or $PtS_2$ as a catalyst. A 2,2,2-trichloroethyl group may be removed using Zn in acetic acid.

Method C Compounds of formula I wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and $Z-R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and

wherein $R_7$=H or alkyl; may be prepared from compounds of formula IV

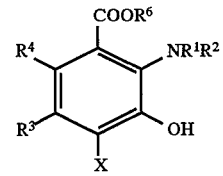

wherein $R^1$, $R^2$, X, $R^3$ and $R^4$ are as defined in formula I in method C and $R^6$ is selected from alkyl, Bn, SEM, MEM, MOM and 2,2,2-trichloroethyl, by deesterifying with for example a base such as KOH in a suitable solvent such as MeOH at room temperature or at elevated temperature, or by alkyl- or arylSLi or alkyl- or arylSNa or with $Me_3SiI$ followed by adjustment of the pH to obtain the 3-hydroxyanthranilic acid deivative. In the case where $R^6$=Bn, the carboxylic acid may be obtained by hydrogenolysis with for example $H_2$ and Pd/C or $PtS_2$. A 2,2,2-trichloroethylester may be cleaved with for example Zn in HOAc and a SEM-ester for example with TBAF in DMPU.

Method D Compounds of formula I wherein $R^1$ and $R^2$ are the same or different and selected from H and alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl; may be prepared from compounds of formula V

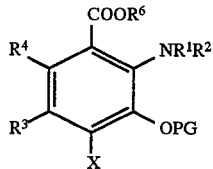

wherein $R^1$, $R^2$, X, $R^3$ and $R^4$ are as defined in formula I in method D; PG and $R^6$ are selected from alkyl, Bn, SEM, MEM and MOM, by deesterification and deprotection with for example alkyl- or arylSLi, alkyl- or arylSNa or with $Me_3$SiI followed by adjustment of the pH to obtain the 3-hydroxyanthranilic acid derivative. In the case where PG and $R^6$=Bn, the 3-hydroxyanthranilic acid derivative may be obtained by hydrogenolysis with for example $H_2$ and Pd/C or $PtS_2$ and if PG and $R^6$=SEM, TBAF may be used.

Method E Compounds of formula I wherein $R^1$=alkyl; $R^2$=H or alkyl; X is selected from alkylthio, arylthio, aryloxy, halogen and cyano; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl; may be prepared from compounds of formula VI

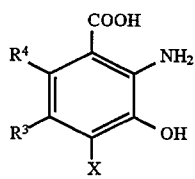

wherein X, $R^3$ and $R^4$ are as defined in formula I in method E, by reductive alkylation with for example an aldehyde corresponding to $R^1$ and a reducing agent such as $NaCNBH_3$ and HCl in a suitable solvent such as $CH_3CN$, $H_2O$ or MeOH. Mono- and di-N-alkylated derivatives can be separated for example by chromatography.

Method F Compounds of formula I wherein $R^1$ and $R^2$ are the same or different and selected from H and alkyl; X is selected from alkylthio, halogen and cyano; $R^3$ is selected from chloro, bromo and iodo; $R^4$ is selected from alkoxy, alkyl, alkylthio, cyano, fluoroalkyl, halogen, $RSO_2$ and RCO wherein R=$C_1$-$C_5$ alkyl, may be prepared from compounds of formula VII

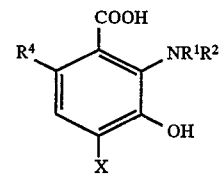

wherein $R^1$, $R^2$, X and $R^4$ are as defined in formula I in method F, by halogenation with for example $Br_2$, $Cl_2$ or ICl in acetic acid at room- or elevated temperature. Alternatively, VII could be halogenated with $Br_2$ or $I_2$ and mercuric trifluoroacetate in trifluoroacetic acid at room- or elevated temperature.

Method G Compounds of formula I wherein $R^1$ and $R^2$ are the same or different and selected from H and alkyl; X is selected from alkylthio, halogen and cyano; $R^3$ is selected from alkoxy, alkyl, alkylthio, cyano, fluoroalkyl, halogen, $RSO_2$ and RCO wherein R=$C_1$-$C_5$ alkyl; $R^4$ is selected from chloro, bromo and iodo, may be prepared from compounds of formula VIII

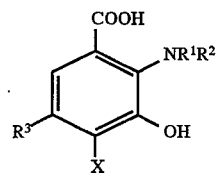

wherein $R^1$, $R^2$, X and $R^3$ are as defined in formula I in method G, by halogenation for example according to method F.

Method H Compounds of formula I wherein $R^1$ and $R^2$ are the same or different and selected from H and alkyl; X is selected from bromo, chloro and iodo; $R^3$, $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl and fluoroalkyl; or $R^3$ and $R^4$ together form a saturated ring system Y-V-Z wherein Y and Z, independently of each other, are as defined for Z above and V is selected from $C_1$-$C_3$ alkylene —N=, —N=N— and

wherein $R_7$=H or alkyl; may be prepared from compounds of formula IX

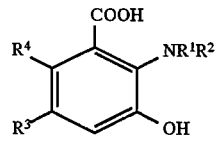

wherein $R^1$, $R^2$, $R^3$ and $R^4$ are as defined in formula I in method H, by halogenation for example according to method F.

INTERMEDIATES

Method II:a Compounds of formula II wherein X is selected from akylthio, arylthio, aryloxy, halogen and cyano; $R^3$ and $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$, $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and

wherein $R_7$=H or alkyl; may be prepared from compounds of formula X

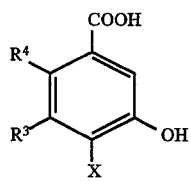

X wherein X, $R^3$ and $R^4$ are as defined in formula II in method II:a, by nitration using for example $HNO_3$ in a solvent such as $CH_3NO_2$, $CH_2Cl_2$ or $H_2O$ or a mixture of $HNO_3$ and $H_2SO_4$.

Method II:b Compounds of formula II wherein X is selected from chloro, bromo and iodo; $R^3$ and $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl and fluoroalkyl; or $R^3$,$R^4$ together form a saturated ring system Y-V-Z wherein Y and Z, independently of each other, are as defined for Z above and V is selected from $C_1$–$C_3$ alkylene or alkenylene, —N=, —N=N— and —N—$R_7$ wherein $R_7$=H or alkyl may be prepared from compounds of formula XI

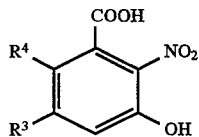

XI wherein $R^3$ and $R^4$ are as defined in formula II in method II:b, by halogenation for example according to method F.

Method III:a Compounds of formula III wherein $R^1$ and $R^2$=H; X is selected from halogen and aryloxy; $R^3$ and $R^4$ are the same or different and selected from halogen, methyl, fluoroalkyl and Z-$R^5$ wherein Z is selected from $CH_n$, $NH_m$, O and $SO_2$ wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$–$C_3$ alkylene or alkenylene, —N=, —N=N— and

wherein $R_7$=H or alkyl; and PG is selected from alkyl, Bn, MEM and MOM; may be prepared from compounds of formula XII

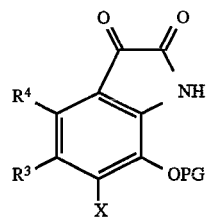

XII wherein X, $R^3$, $R^4$ and PG are as defined in formula III in method III:a by reacting a compound of formula XII with for example $H_2O_2$ and NaOH in a suitable solvent such as water or dioxan. The pH is then adjusted to obtain the 3-hydroxyanthranilic acid derivative.

Method III:b Compounds of formula III wherein $R^1$ and $R^2$=H; X is selected from alkylthio, chloro and fluoro; $R^3$ and $R^4$ are the same or different and selected from chloro, fluoro, methyl, fluoroalkyl and Z-$R^5$ wherein Z is selected from $CH_n$, N, O and S wherein n=1 or 2; and $R^5$=alkyl; or $R^3$ and $R^4$ together form a saturated or unsaturated ring system Y-V-Z wherein Y and Z; are as defined for Z above and V is selected from $C_1$–$C_3$ alkylene or alkenylene, —N=, —N=N— and

wherein $R_7$=H or alkyl; and PG is selected from alkyl, SEM, MEM and MOM; may be prepared from compounds of formula XIII

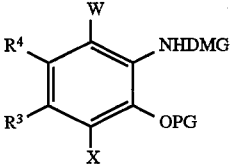

XIII wherein X, $R^3$, $R^4$ and PG are as defined in formula III in method III:b; DMG=COtBu, $CO_2$tBu or $COCF_3$; W=H or Br for example by reaction with alkyllithium in a suitable solvent such as tetrahydrofuran (THF) at low temperature. The aryllithium derivative is then reacted with $CO_2$(s), acidified and the DMG group is removed by aqueous HCl at elevated temperature.

Method IV:a Compounds of formula IV wherein $R^1$ and $R^2$ are the same or different and selected from H and alkyl; X is selected from alkylthio, halogen and cyano; $R^3$ is selected from chloro, bromo and iodo; $R^4$ is selected from alkoxy, alkyl, alkylthio, cyano, fluoroalkyl, halogen, $RSO_2$ and RCO wherein R=$C_1$–$C_5$ alkyl; $R^6$ is for example selected from SEM, MEM, MOM and 2,2,2-trichloroethyl; may be prepared from compounds of formula XIV

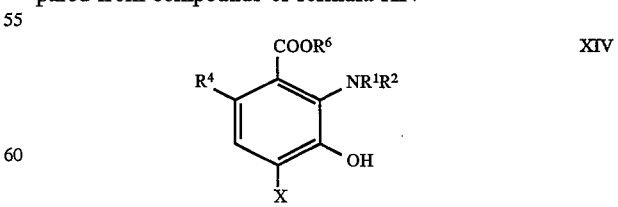

wherein $R^1$, $R^2$, X, $R^4$ and $R^6$ are as defined in formula IV in method IV:a; by halogenation for example according to method F.

Method IV:b Compounds of formula IV wherein $R^1$=H or alkyl; $R^2$ =alkyl; X is selected from alkylthio, arylthio, aryloxy, halogen and cyano; $R^3$ and $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$, $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl; $R^6$ is selected from SEM, MEM, MOM and 2,2,2-trichloroethyl; may be prepared from compounds of formula XV

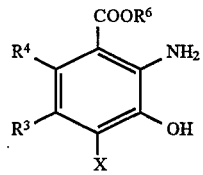

XV wherein X, $R^3$, $R^4$ and $R^6$ are as defined in formula IV in method IV:b; by alkylation for example according to method E.

Method V Compounds of formula V wherein $R^1$ and $R^2$ are the same or different and selected from H and alkyl; X is selected from alkylthio, arylthio, aryloxy, chloro, fluoro and cyano; $R^3$, $R^4$ are the same or different and selected from chloro, fluoro, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$, $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl; $R^6$ and PG are selected from alkyl and Bn; may be prepared from compounds of formula XVI

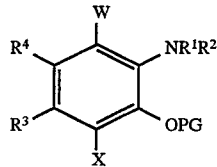

XVI wherein $R^1$, $R^2$, X, $R^3$, $R^4$ and PG are as defined in formula V in method V and W=Br, I or $OSO_2CF_3$ by reacting a compound of formula XVI with for example a mixture of $Pd(OAc)_2$, CO, 1,3-bis(diphenylphosphino)-propane and an alcohol corresponding to $R^6$ in a suitable solvent such as DMF or dioxan containing a base such as $Et_3N$.

Method VI Compounds of formula VI wherein X is selected from alkylthio, arylthio, aryloxy, halogen and cyano; $R^3$ and $R^4$ are the same or different and selected from halogen, methyl, fluoroalkyl, cyano and Z-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$, $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl; may be prepared from compounds of formula XVII

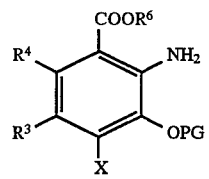

XVII wherein X, $R^3$ and $R^4$ are as defined in formula VI in method VI and $R^6$ and PG are selected from alkyl, Bn, SEM, MEM and MOM; by deesterifying and deprotecting for example according to method D.

Method VII:a Compounds of formula VII wherein $R^1$ and $R^2$=H; X is selected from alkylthio, arylthio, aryloxy, halogen and cyano; $R^4$=$RSO_2$ or RCO wherein R=$C_1$-$C_5$ alkyl; may be prepared from compounds of formula XVIII

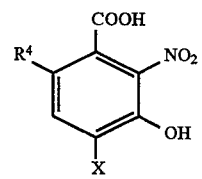

XVIII wherein X and $R^4$ are as defined in formula VII in method VII:a; by reduction for example according to method A.

Method VII:b Compounds of formula VII wherein $R^1$ and $R^2$ are the same or different and selected from H and alkyl; X is selected from alkylthio, arylthio, aryloxy, halogen and cyano; $R^4$=$RSO_2$ or RCO wherein R=$C_1$-$C_5$ alkyl may be prepared from compounds of formula XIX

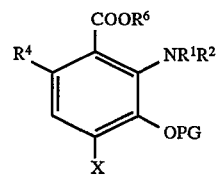

XIX wherein $R^1$, $R^2$, X and $R^4$ are as defined in formula VII in method VII:b and $R^6$ and PG are selected from alkyl, Bn, SEM, MEM and MOM; by deesterifying and deprotecting for example according to method D.

Method VIII Compounds of formula VIII wherein $R^1$ and $R^2$ are the same or different and selected from H and alkyl; X is selected from chloro, bromo and iodo; $R^3$ is selected from $RSO_2$ and RCO wherein R=$C_1$-$C_5$ alkyl, may be prepared from compounds of formula XX

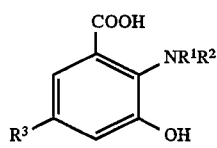

XX wherein $R^1$, $R^2$ and $R^3$ are as defined in formula VIII in method VIII, by halogenation for example according to method F.

Method IX:a Compounds of formula IX wherein $R^1$ and $R^2$ are the same or different and selected from H and alkyl; $R^3$ is selected from chloro, bromo and iodo; $R^4$ is selected from alkoxy, alkyl, alkylthio, cyano, fluoroalkyl, halogen, $RSO_2$ and RCO, may be prepared from compounds of formula XXI

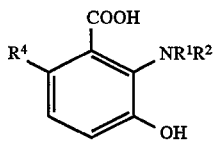

XXI wherein $R^1$, $R^2$ and $R^4$ are as defined in formula IX in method IX:a, by halogenation for example according to method F.

Method IX:b Compounds of the formula IX wherein $R^1$ and $R^2$ are the same or different and selected from H and alkyl; $R^3$ and $R^4$ are the same or different and selected from halogen, methyl, fluoroalkyl, cyano and $Z-R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$, $R^4$ together form a saturated or unsaturated ring system Y-V-Z wherein Y and Z, independently of each other, are as defined for Z above and V is selected from $C_1-C_3$ alkylene or alkenylene, —N═, —N═N— and

wherein $R_7$=H or alkyl; may be prepared from compounds of formula XXII

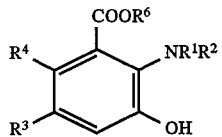

XXII wherein $R^1$, $R^2$, $R^3$ and $R^4$ are as defined in formula IX in method IX:b and $R^6$ is selected from alkyl, Bn, SEM, MEM, MOM and 2,2,2-trichloroethyl, by deesterifying for example according to method C.

WORKING EXAMPLES

Example 1 (Method B)

Preparation of 4-Chloro-5,6-dimethyl-3-hydroxyanthranilic acid

2-Chloro-3,4-dimethyl-6-nitrophenol 4,5-Dimethyl-2-nitrophenol[1] (7.00 g, 41.9 mmol) was dissolved in $CHCl_3$ (300 mL) and flushed with argon. Chlorine, dissolved in $CHCl_3$ (84.8 mL, 0.99M, 83.7 mmol) was added and the solution was stirred at room temperature for 26 h, protected from light. The solvent, HCl and excess of $Cl_2$ were evaporated (protected from light) and the residue was partitioned between $CH_2Cl_2$ (400 mL) and brine (100 mL). Drying ($MgSO_4$) and evaporation of the solvent gave 8.9 g of a crude product. Purification by flash column chromatography ($SiO_2$, $CHCl_3$-Hexane 1:1) afforded the title compound (6.47 g) Mp: 62°–63° C.; $^1H$ NMR (DMSO-$d_6$): δ 11.5 (br, OH), 7.80 (s, 1 H), 2.34 (s, 3 H), 2.27 (s, 3 H); $^{13}C$ NMR (DMSO-$d_6$): δ 146.86, 143.84, 134.06, 128.85, 123.73, 122.94, 19.37, 17.36; MS (EI, 70 eV): m/z (rel.int.) 203/201 ($M^+$, 37/100), 91 (88).

1-Benzyloxy-2-chloro-3,4-dimethyl-6-nitrobenzene

2-Chloro-3,4-dimethyl-6-nitrophenol (6.44 g, 31.9 mmol) was dissolved in dry DMF (105 mL) and flushed with argon. Benzyl bromide (4.17 mL,35.1 mmol) and $K_2CO_3$ (13.24 g, 95.7 mmol) were added. The reaction mixture was stirred at room temperature for 8 h (protected from light) and filtered. Water (5 mL) was added and the solvent was co-evaporated with xylene (2×150 mL) and $CH_2Cl_2$ (100 mL). The residue was mixed with $CHCl_3$ (100 mL), filtered and after evaporation of the solvent 10.8 g of crude product remained. Purification by flash column chromatography ($SiO_2$, $CHCl_3$-Hexane 1:1) gave the title compound (8.44 g). Mp: 74°–75° C.; $^1H$ NMR (DMSO-$d_6$): δ 7.80 (s, 1 H), 7.48–7.37 (m, 5 H), 5.06 (s, 2 H), 2.37 (s, 3 H), 2.34 (s, 3 H); $^{13}C$ NMR (DMSO-$d_6$): δ 145.24, 142.22, 142.08, 135.73, 134.73, 129.61, 128.39, 128.37, 128.35, 123.64, 75.74, 19.74, 17.13; MS (EI, 70 eV): m/z (rel.int.) 293/291 ($M^+$, 0.08/0.37), 187/185 (8/24), 91 (100).

6-Amino-1-benzyloxy-27chloro-3,4-dimethylbenzene

1-Benzyloxy-2-chloro-3,4-dimethyl-6-nitrobenzene (3.00 g, 10.3 mmol) was dissolved in MeOH (420 mL) and cooled to +2° C. Copper(I) chloride (6.11 g, 30.8 mmol) was added followed by $KBH_4$ (3.88 g, 72.0 mmol) portionwise added at +2° to +4° C. during 1.5 h. The reaction mixture was stirred at +2° C. for 1 h and more $KBH_4$ (400 mg, 7.41 mmol) was added. After 1 h at +2° C. additional $KBH_4$ (120 mg, 2.22 mmol) was added and the stirring was continued for another 20 min. Filtration and evaporation of the solvent gave a residue which was extracted between EtOAc (400 mL) and water (75 mL). Drying ($MgSO_4$) and evaporation afforded 2.94 of crude product. Purification by flash column chromatography ($SiO_2$, $CHCl_3$) yielded the title compound (2.14 g). Mp: 57°–58° C.; $^1H$ NMR(DMSO-$d_6$): δ 7.54 (d, J=6.5 Hz, 2 H), 7.42–7.34 (m, 3 H), 6.52 (s, 1 H),4.83 (s, 2 H), 4.79 (s, 2 H), 2.12 (s, 6 H); $^{13}C$ NMR (DMSO-$d_6$): δ 140.00, 138.91, 137.30, 133.00, 128.27, 128.22, 127.91, 127.33, 121.23, 115.35, 72.73, 20.24, 15.45; MS (EI, 70 eV): m/z (rel.int.) 286/284 (M+23,42/100).

1-Benzyloxy-2-chloro-3,4-dimethyl-6-(E/Z)-isonitrosoacetamidobenzene

6-Amino-1-benzyloxy-2-chloro-3,4-dimethylbenzene (2.14 g, 8.1.9 mmol) was dissolved in DMF (60 mL) and water (2 mL). Concentrated HCl (683 μL, 8.19 mmol) and chloral hydrate (1.49 g, 9.00 mmol) were added and the flask was placed in an oil-bath preheated to 105° C. After 2 min $NH_2OH.HCl$ (2.28 g, 32.8 mmol), dissolved in water (4 mL) was added and the reaction mixture was stirred at 100° C. for 1 h, protected from light and for 15 min at room temperature. Evaporation and co-evaporation with xylene and $CH_2Cl_2$ gave a residue which was extracted between EtOAc and water. After drying the organic phase ($MgSO_4$) and evaporation of the solvent 3.2 g of crude product was obtained. Purification by flash column chromatography ($SiO_2$, EtOAc-$CHCl_3$ 1:10) afforded an E/Z mixture of the title compound (1.278 g). $^1H$ NMR (DMSO-$d_6$): δ 12.33 and 9.71 (2 s, 1 H), 9.20 and 8.27 (2 s, 1 H), 7.91 and 7.83 (2 s, 1 H), 7.60 (s, 1H), 7.65–7.36 (m, 5 H), 4.90 and 4.87 (2 s, 2 H), 2.26–2.23 (m, 6 H); $^{13}C$ NMR (DMSO-$d_6$): δ 160.18, 159.99, 143.40, 143.06, 136.55, 136.08, 133.40, 133.26, 130.97, 130.39, 129.70, 129.44, 128.69, 128.40, 128.36, 128.28, 128.19, 128.11, 128.03, 127.37, 127.25, 121.51, 121.21, 74.66, 74.18, 20.32, 16.08; MS (EI, 70 eV): m/z (rel.int.).334/332 ($M^+$, 4/12), 172/170 (12/51), 91(100).

7-Benzyloxy-6-chloro-1H-4,5-dimethylbenzindole-2,3-dione

Concentrated $H_2SO_4$ (6 mL) was heated to 80° C. and 1-benzyloxy-2-chloro-3,4-dimethyl-6-(E/Z)-isonitrosoacetamidobenzene (700 mg, 2.10 mmol) was added. The reaction mixture was stirred at 80° C. for 10 min and poured into ice-water (200 mL). Extraction with EtOAc (200 mL), drying ($MgSO_4$) and evaporation gave a residue 376 mg was dissolved in dry DMF (5 mL) and BnBr (275

μL, 2.30 mmol) and K$_2$CO$_3$ (318 mg, 2.30 mmol) were added. The reaction mixture was stirred for 30 h at room temperature protected from light. Filtration, addition of HOAc (1 mL), co-evaporation with xylene (3×100 mL), mixing the residue with HOAc (500 μL) and CH$_2$Cl$_2$-MeOH (50:1, 15 mL), filtration again and evaporation gave 741 mg of crude product. Purification by repeated flash column chromatography (SiO$_2$, CH$_2$Cl$_2$-MeOH-gradient) gave the title compound (13 mg). $^1$H NMR (DMSO-d$_6$): δ 11.42 (s, 1 H), 7.57 (d, J=6.2 Hz, 2 H), 7.42–7.35 (m, 3 H), 4.92 (s, 2 H), 2.44 (s, 3 H), 2.22 (s, 3H); $^{13}$C NMR (DMSO-d$_6$): δ 184.30, 159.33, 141.87, 137.02, 136.98, 136.26, 135.41, 130.15, 128.84, 128.28, 128.18, 115.64, 74.63, 15.26, 14.20; MS (EI, 70 eV): m/z (rel.int.) 317/315 (M$^+$, 3/7), 91 (100).

3-Benzyloxy-4-chloro-5,6-dimethylanthranilic acid

7-Benzyloxy-6-chloro-1H-4,5-dimethylbenzindole-2,3-dione (13 mg, 0.04 mmol) was mixed with dioxan (500 μL) and NaOH (200 μL, 0.68M, 0.14 mmol) was added. The solution was cooled to +10° C. and H$_2$O$_2$ (4 μL, 30%, 0.12 mmol) dissolved in NaOH (410 μL, 0.68M, 0.27 mmol) was added. More H$_2$O$_2$ (1 μL, 0.03 mmol) was added after 2 min and the reaction mixture was stirred for 1 h at room temperature. Hydrogen peroxide (2 μL, 0.06 mmol) was added and after 20 min some of the solvent was removed by a stream of N$_2$ before HOAc (38 μL, 0.66 mmol) was added precipitating a crude orange product. As much dioxan as possible was removed before the slurry was partitioned between EtOAc (3 mL) and water (500 μL), the aqueous phase was extracted with EtOAc (500 μL) and the combined organic phase was washed with brine (500 μL) and dried (MgSO$_4$). After evaporation of the solvent the residue was dissolved in dioxan (100 μL) and NaOH (200 μL, 0.68M, 0.14 mmol), cooled to +10° C. and reacted with H$_2$O$_2$ (4 μL, 0.12 mmol) in NaOH (400 μL, 0.27 mmol) for 3 h at +10° C. to room temperature. Work-up as described above gave the title compound (11 mg). $^1$H NMR (DMSO-d$_6$): δ 7.55 (d, J=7.0 Hz, 2 H),7.43–7.35 (m, 3 H), 4.82 (s, 2 H), 2.21 (s, 3 H), 2.19 (s, 3 H); MS (EI, 70 eV): m/z (rel.int.) 307/305 (M$^+$, 7/19), 216/214 (26/75), 198/196(14/44), 91(100).

4-Chloro-5,6-dimethyl-3-hydroxyanthranilic acid

3-Benzyloxy-4-chloro-5,6-dimethylanthranilic acid (10 mg, 0.03 mmol) was dissolved in EtOH (1.5 mL) and 10% Pd/C (2 mg) was added. Hydrogenation at room temperature and atmospheric pressure for 5 h, filtration, evaporation yielded 7 mg of crude product. Purification by preparative HPLC (Lichrosorb-C$_{18}$, MeOH-Phosphate buffer (pH3) 50:50) adjusting the pH to 5 with NaHCO$_3$ (aq), concentrating by a stream of N$_2$, extracting with EtOAc (3×5 mL), washing the organic phase with brine, drying (MgSO$_4$) and evaporating afforded the title compound (3 mg). $^1$H NMR (DMSO-d$_6$): δ 3.3 (br, OH), 3.16 (s, 2 H), 2.16 (s, 3 H), 2.15 (s, 3 H); $^{13}$C NMR (DMSO-d$_6$): δ 169.92, 137.87, 135.16, 126.38, 123.51, 121.39, 117.31, 17.72, 15.95; MS (EI, 70 eV): m/z (rel.int.) 217/215 (M$^+$, 21/63),199/197 (20/59), 171/169 (37/100).

Example 2 (Method B)

Preparation of 7-Amino-5-chloro-8-carboxy-6-hydroxytetralin

5-Chloro-6-hydroxy-7-nitrotetralin

6-Hydroxy-7-nitrotetralin[2] (2.44 g, 12.6 mmol) was dissolved in CHCl$_3$ (290 mL) and the solution was flushed with argon. Chlorine, dissolved in CHCl$_3$ (25.6 mL, 0.99M, 25.3 mmol) was added and the solution was stirred for 6 h at room temperature, protected from light. The solvent, HCl and excess of Cl$_2$ were evaporated protected from light giving 3.02 g of crude product. Purification by flash column chromatography (SiO$_2$, CHCl$_3$-Hexane 1:1) gave the title compound (2.29 g). $^1$H NMR (DMSO-d$_6$): δ 10.62 (br, 1 H), 7.71 (s, 1 H), 2.75–2.69 (m, 4 H), 1.77–1.64 (dm, 4H); $^{13}$C NMR (DMSO-d$_6$): δ 146.30, 143.58, 134.59, 129.68, 123.42, 122.79, 28.26, 27.91, 21.69, 21.62; MS (EI, 70 eV): m/z (rel.int.) 229/227 (M$^+$, 32/100, 101/99 (12/36), 117/115 (23/50).

6-Benzyloxy-5-chloro-7-nitrotetralin

5-Chloro-6-hydroxy-7-nitrotetralin (2.28 g, 10.0 mmol) was dissolved in dry DMF (40 mL) and flushed with argon. Benzyl chloride (11.5 mL, 100.0 mmol) n-Bu$_4$NI (95 mg, 0.25 mmol) and K$_2$CO$_3$ (41.5 g, 30.0 mmol) were added. The reaction mixture was stirred for 24 h at room temperature, protected from light. The salts were filtered off and the solvent and excess of BnCl were co-evaporated with xylene (3×200 mL) and CH$_2$Cl$_2$ (200 mL), followed by vacuum-drying. The crude product (5.8 g) was purified by flash column chromatography (SiO$_2$, CHCl$_3$-Hexane 1:1) and afforded the title compound (2.20 g). Mp 80°–82° C.; $^1$H NMR (DMSO-d$_6$): δ 7.73 (s, 1 H), 7.48–7.37 (m, 5 H), 5.06 (s,2 H), 2.79–2.75 (m, 4 H), 1.79–1.69 (dm, 4 H); $^{13}$C NMR (DMSO-d$_6$): δ 144.81, 142.14, 135.79, 135.56, 129.55, 128.42, 123.40, 106.20, 105.51, 75.80, 28.63, 27.65, 21.55, 21.36; MS (TSP): m/z (rel.int.) 337/335 (M+NH$_4$, 30/100).

7-Amino-6-benzyloxy-5-chlorotetralin

Methanol (430 mL) was added to 6-benzyloxy-5-chloro-nitrotetralin (2.56 g, 8.33 mmol) and the mixture was cooled to +1° C. Copper(I) chloride (4.95 g, 25.0 mmol) was added followed by portionwise addition of KBH$_4$ (3.15 g, 58.3 mmol) during 1 h 10 min at +2° C. After 3.5 h more KBH$_4$ (100 mg, 1.85 mmol) was added and after 7.5 h at +2° C., the reaction mixture was filtered and the solvent evaporated. The residue was extracted between EtOAc and water and the organic phase was washed with brine (50 mL), dried (Na$_2$SO$_4$) and evaporated giving 2.47 g of crude product. Purification by flash column chromatography (SiO$_2$, CHCl$_3$) yielded the title compound (1.82 g). $^1$H NMR (DMSO-d$_6$): δ 7.55 (dd, J$_1$=1.6 Hz, J$_2$=8.1 Hz, 2 H), 7.41–7.34 (m, 3 H), 6.42 (s, 1 H), 4.84 (s, 2 H), 4.79 (s, 2 H), 258–2.52 (m, 4 H), 1.71–1.60 (m, 4 H); $^{13}$C NMR (DMSO-d$_6$) d 140.10, 139.29, 137.29, 133.96, 128.29, 128.23, 127.93, 126.99, 121.84, 113.96, 29.03, 26.25, 22.68, 22.35; MS (TSP): m/z (rel.int.) 290/288 (M+1, 27/100).

6-Benzyloxy-5-chloro-7-(E/Z)-isonitrosoacetamidotetralin

7-Amino-6-benzyloxy-5-chlorotetralin (1.84 g, 6.41 mmol) was dissolved in DMF (80 mL) and water (8 mL). The solution was flushed with argon and HCl (530 μL, 12M, 6.41 mmol) was added followed by chloral hydrate (1.17 g, 7.05 mmol). The flask was placed in an oil-bath, preheated to 110° C. and a solution of NH$_2$OH.HCl (1.78 g, 25.6 mmol) in water (8 mL) was added under stirring. After 1 h at 100° C. followed by 1 h at room temperature, the solvents were co-evaporated with xylene (3×100 mL) and CH$_2$Cl$_2$ (100 mL). The residue was extracted between EtOAc and water and the organic phase was washed with brine (50 mL), dried (Na$_2$SO$_4$) and evaporated yielding 2.63 g of crude product. Purification by flash column chromatography (SiO$_2$, EtOAc-CHCl$_3$ 1:5) afforded an E/Z mixture of the title compound. $^1$H NMR(DMSO-d$_6$): δ 12.33 and 9.72 (2 s, 1 H), 9.20 and 8:28 (2 s, 1 H), 7.84 and 7.72 (2 s, 1 H), 7.60 (s, 1 H), 7.57–7.37 (m, 5 H), 4.90 and 4.88 (2 s, 2 H), 2.71–2.65 (m, 4 H), 1.75–1.68 (m, 4 H); $^{13}$C NMR (DMSO-d$_6$): δ 160.26, 160.02, 143.45, 143.00, 136.60, 136.13, 134.37, 134.26, 131.20, 130.63, 129.81, 129.52, 128.75, 128.33, 128.16, 128.09, 127.04, 120.68, 120.33, 74.75, 74.28, 29.13, 26.74, 22.17, 22.00; MS(TSP): m/z (rel.int.) 361/359 (M+1, 28/100).

9-Benzyloxy-8-chloro-1H-4,5,6,7-tetrahydro[e]benzindole-2,3-dione

Concentrated $H_2SO_4$ (5 mL) was heated to 60° C. and 6-benzyloxy-5-chloro-7-(E/Z)-isonitrosoacetamidotetralin (500 mg, 1.39 mmol) was added portionwise during 1 min. The reaction mixture was stirred at 60° C. for 10 min and poured on crushed ice (50 mL). Extraction with EtOAc (200 mL), drying ($Na_2SO_4$) and evaporation gave a residue 317 mg which was dissolved in dry DMF (3 mL) and flushed with argon. Benzyl bromide (165 μL, 1.39 mmol) and $K_2CO_3$ (192 mg, 1.39 mmol) were added and the reaction mixture was stirred at room temperature for 18 h. Methanol (3 mL) was added, the salts were filtered off, and the solvents were co-evaporated with xylene (2×30 mL) followed by drying in vacuum. Acetic acid (0.3 mL, 5.2 mmol) was added to the crude product and filtration through $SiO_2$ using (EtOAc-MeOH 20:1) as eluent followed by evaporation of the solvents gave a dark residue (330 mg). Purification by repeated flash column chromatography ($SiO_2$, $CH_2Cl_2$-MeOH 50:1) afforded the title compound (56 mg). $^1H$ NMR (DMSO-$d_6$): δ 11.40 (s, 1 H), 7.58 (d, J=7.3 Hz, 2 H), 7.42–7.36 (m, 3 H), 4.90 (s, 2 H), 2.92 (t, J=7.3 Hz, 2 H), 2.63(t, J=6.0 Hz, 2 H), 1.74–1.66 (m, 4 H); $^{13}C$ NMR (DMSO-$d_6$): δ 183.83, 159.39, 142.27, 137.26, 137.05, 136.25, 136.20, 129.90, 128.76, 128.22, 128.13, 114.74, 74.63, 26.68, 25.42, 21.71, 20.77; MS (EI, 70 eV) m/z (rel.int.) 343/341 ($M^+$, 5/15), 91 (100).

7-Amino-6-benzyloxy-8-carboxy-5-chlorotetralin

9-Benzyloxy-8-chloro-1H-4,5,6,7-tetrahydro[e]-benzindole-2,3-dione (51 mg, 0.15 mmol) was mixed with NaOH(aq) (890 μL, 0.68M, 0.60 mmol), water (460 μL) was added and the slurry was cooled to +10° C. Hydrogen peroxide (46 μL, 30%, 0.45 mmol) was mixed with NaOH (aq) (1.33 mL, 0.68M, 0.90 mmol) and added to the slurry. After 2 min more $H_2O_2$ (20 μL, 30%, 0.20 mmol) was added and the reaction mixture was stirred for 1 h at room temperature. Dioxan (1.5 mL) was added to the slurry followed by additional $H_2O_2$ (20 μL, 30%, 0.20 mmol) and stirred for another 2 h. The solution was filtered diluted with water (2 mL) and HOAc (100 μL, 1.75 mmol) was added precipitating the product. After stirring the slurry for 30 min EtOAc (40 mL) and water (10 mL) were added. Extracting the aqueous phase with EtOAc (10 mL) and washing the combined organic layer with brine (10 mL), drying ($Na_2SO_4$) and evaporating yielded the title compound (35 mg). $^1H$ NMR (DMSO-$d_6$): δ 7.56 (d, J=7.0 Hz, 2 H), 7.43–7.36 (m, 3 H), 4.84 (s, 2 H) 3.3 (br, NH, OH), 2.73 (m, 2 H), 2.59 (m, 2 H), 1.70–1.61 (m, 4 H); $^{13}C$ NMR (DMSO-$d_6$): δ 169.29, 139.87, 139.47, 136.83, 133.13, 129.46, 128.28, 128.25, 128.05, 122.28, 116.49, 73.08, 28.08, 26.76, 22.17, 22.04; MS (EI, 70 eV): m/z (rel.int.) 333/331 ($M^+$, 7/18); 224/222 (22/63), 91 (100).

7-Amino-5-chloro-8-carboxy-6-hydroxytetralin

7-Amino-6-benzyloxy-8-carboxy-5-chlorotetralin (33 mg, 0.10 mmol) was dissolved in EtOH (3 mL) and 5% Pd/C (4 mg) was added. Hydrogenation at room temperature and atmospheric pressure for 2 h, filtration, evaporation and vacuum-drying gave the title compound (21 mg). Mp: 147° C. (dec); $^1H$ NMR (DMSO-$d_6$): δ 7.9 (br, NH, OH), 2.66 (t, J=6.0 Hz, 2 H), 2.54 (t, J=6.7 Hz, 2 H), 1.70–1.64 (m, 2 H), 1.63–1.57(m, 2 H) ; $^{13}C$ NMR (DMSO-$d_6$): δ 169.73, 138.12, 136.45, 128.13, 123.32, 121.36, 115.15, 27.86, 26.91, 22.45, 22.25; MS (EI, 70 eV): m/z (rel.int.) 243/241 ($M^+$, 21/65), 225/223 (35/100), 197/195 (61/100).

Example 3 (Method A)

Preparation of 4,6-dichloro-3-hydroxy-5-methylanthranilic acid 2,4-Dichloro-5-methoxy-3-methylphenyl triflate 2,4-Dichloro-5-methoxy-3-methylphenol[3] (7.73 g, 37.3 mmol) was dissolved in $CH_2Cl_2$ (180 mL) and flushed with argon. Triethylamine (10.4 mL, 74.7 mmol) and DMAP (10 mg, 0.08 mmol) were added. The solution was cooled to −78° C. and trifluoromethane sulfonic anhydride (9.4 mL, 56.0 mmol) was added dropwise during 3 min. After 10 min at −78° C. the reaction vessel was placed in an ice-bath and the stirring continued for additional 10 min. Methylene chloride (200 mL) and $H_2O$ (150 mL) were added. The aqueous phase was extracted with $CH_2CL_2$ (150 mL) and the combined organic phase was washed with brine (100 mL) and dried ($MgSO_4$). Evaporration of the solvent gave 20 g of a crude product. Filtration through $SiO_2$ using $CH_2Cl_2$ as the eluent followed by flash column chromatography ($SiO_2$, EtOAc-Hexane 1:3) aforded 12.3 g of the pure title compound. Mp: 74° C.; $^1H$ NMR(DMSO-$d_6$): δ 7.30 (s, 1H), 3.92 (s, 3H), 2 49 (s, 3H); $^{13}C$ NMR (DMSO-$d_6$): δ 154.23, 143.90, 136.95, 122.78, 118.07, 118.04 (q, d=321 Hz), 105.36, 57.22, 18.01; MS (EI, 70 eV); m/z (rel.int.) 340/338 ($M^+$, 47/64), 207/205 (27/41),179/177 (64/100).

Methyl 2,4-dichloro-5-methoxy-3-methylbenzoate 2,4-Dichloro-5-methoxy-3-methylphenyl triflate (7.60 g, 22.4 mmol) was dissolved in dioxan (75 mL), 1,3-bis (diphenylphosphino)propane (371 mg, 0.90 mmol) and palladium acetate (202 mg, 0.90 mmol) were added. After flushing with CO, $Et_3N$ (6.90 mL, 49.4 mmol) and MeOH (23 mL) were added. Reaction with CO at 70° C. and at atmospheric pressure for 25° C., filtration and evaporation, of the solvent partition of the residue between $Et_2O$ (350 mL) and 3M $NH_3$ (150 mL), extraction of the aqueous layer with $Et_2O$ (2×150 mL) followed by washing the combined organic phase with brine (150 mL), drying ($MgSO_4$), evaporation of the solvent gave a crude product. Filtration through $SiO_2$ using EtOAc as the eluent gave 5.2 g of a product which was purified by flash column chromatograhy ($SiO_2$, EtOAc-Hexane 1:3) to yield 4.18 g of the title compound. Mp: 74° C.; $^1H$ NMR(DMSO-$d_6$): δ 7.33 (s, 1H), 3.88 (s, 3H), 3.86 (s, 3H), 2.45 (s, 3H); $^{13}C$ NMR (DMSO-$d_6$) : δ 165.69, 153.26, 136.09, 130.46, 125.22, 122.95, 110.78, 56.64, 52.72, 17.86; MS (EI, 70 eV): m/z (rel.int.) 250/248 ($M^+$, 53/80), 219/217 (66/100), 191/189 (8/12).

2,4-Dichloro-5-hydroxy-3-methylbenzoic acid

Methyl 2,4-dichloro-5-methoxy-3-methylbenzoate (238 mg, 0.96 mmol) was dissolved in MeOH (30 mL) and flushed with argon. Potassium hydroxide (308 mg, 4.78 mmol) was added and the reaction mixture was stirred at 50° C. for 19 h. The solvent was evaporated and the residue was dried in vacuum. Hydrobromic acid 30 mL, 48%, aq) was added and the mixture was heated to 110° C. After 3 days most of the HBr was removed by vacuum-distillation. The crude product was mixed with $H_2O$ (10 mL), concentrated $NH_3$ (1 mL) and EtOAc (40 mL) were added, the aqueous phase (pH 1) was extracted with EtOAc (2×20 mL) and the combined organic phase was washed with brine (10 mL) and dried ($MgSO_4$). Evaporation of the solvent gave 202 mg of the title compound. $^1H$ NMR (DMSO-$D_6$): δ 10.68 (br, 1H), 7.15 (s, 1H), 2.42 (s, 3H); $^{13}C$ NMR (DMSO-$d_6$): δ 166.68, 151.82, 135.87, 131.24, 123.70, 121.17, 114.36, 17.93; MS (EI, 70 eV): m/z (rel.int.) 222/220 ($M^+$, 56/100), 205/203 (36/59), 185(26).

4,6-Dichloro-3-hydroxy-5-methyl-2-nitrobenzoic acid 2,4-Dichloro-5-hydroxy-3-methylbenzoic acid (90 mg, 0.41 mmol) was mixed with $CH_3NO_2$ (9 mL) and heated to 40 °C. To the solution was added HNO$_3$ (20 µL, 90%, 0.43 mmol) and the reaction mixture was stirred at room temperature for 4 h. Evaporation of the solvent followed by vacuum-drying over KOH gave 112 mg of a crude product. Purification by flash column chromatography (SiO$_2$, EtOAc-HOAc 30:1) afforded 79 mg of the title compound. Mp: 199° C. (dec); $^1$H NMR (DMSO-d$_6$): δ 2.45 (s, 3H); $^{13}$C NMR (DMSO-d$_6$): δ 164.27, 147.05, 139.61, 136.27, 128.35, 126.46, 118.87, 18.62; MS (EI, 70 eV): m/z (rel.int.) 267/265 (M$^+$, 66/100), 249/248 (67/85), 205/203 (28/54).

4,6-Dichloro-3-hydroxy-5-methylanthranilic acid 4,6-Dichloro-3-hydroxy-5-methyl -2nitrobenzoic acid (69 mg, 0.26 mmol) was dissolved in HOAc (10 mL), 10% Pd/C (10 mg) and concentrated HCl (33µ, 0.39 mmol) were added. Hydrogenation at room temperature and at atmospheric pressure for 2 h gave a slurry to which methanol (5 mL) was added and the catalyst was filtered off. Evaporation of the solvent, co-evaporation with toluene (10 mL) followed by vacuum-drying over KOH gave 63 mg of a crude product. Purification by flash column chromatography (SiO$_2$), EtOAc-HOAc 45:1) yielded 55 mg of the title compound. Mp: 192° C. (dec); $^1$H NMR (DMSO-d$_6$): δ 2.27 (s, 3H); $^{13}$C NMR (DMSO-d$_6$): δ 167.43, 139.25, 136.01, 122.90, 121.26, 120.37, 116.89, 16.96;MS (EI, 70 eV): m/z (rel.int.) 237/235 (M$^+$, 45/79), 219/217 (37/64), 191/189 (60/100).

References

1. Diepolder E Chem. Ber. 42, 2916, 1909
2. Chudozilov L. K Collect. Czech. Commun 1, 304, 1929
3. Calam CT, J. Chem. Soc., 280, 282, 1939

PHARMACOLOGICAL METHOD

Materials

[Carboxy-$^{14}$C]3-hydroxyanthranilic acid (6 mCi/mmol) was received from Drs. E. Shaskan and L. Spitznagle (University of Connecticut, Farmington, Conn., U.S.A.). [$^3$H]QUIN was obtained from the Nuclear Research Center (Negev, Israel). All other chemicals and reagents were obtained from commercial suppliers.

Tissue Preparations

For routine assays, male Sprague-Dawley rats (150–200 g) were killed by decapitation and their brains rapidly dissected onto ice. Whole forebrains or individual CNS regions were sonicated in four volumes (wt/vol) of distilled water, centrifuged at 50,000 g for 20 min at 4° C., and the resulting supernatant used for the assay. For subcellular fractionation, the method of Mena et al. (1980) was used and the following fractions were collected: P1 (nuclear fraction), P2 (crude synoptosomal fraction), P3 (microsomal fraction), soluble (cytosol fraction), myelin, synaptosomes, and mitochondria. All nonsoluble fractions were sonicated prior to assay.

Measurement of 3-HAO Activity

For routine assays, 20 µl of tissue extract (equivalent to 5 mg of original tissue wet weight) were incubated in the presence or absence of inhibitor (in 10 µl) at 37° C. for 30 min in a solution containing 0.3 mM Fe (SO4)2, 38 mM 4-(2-hydroxyethyl)piperazine-1-ethanesulfonic acid (HEPES)/NaOH buffer (pH 6.0), and 5 µM ([$^{14}$C]3HANA in a total volume of 195 µl. Blank values were obtained under identical conditions using tissue that had been heated for 5 min in a boiling water bath. The incubation was terminated by the addition of 50 µl 6% HClO$_4$, the tubes cooled on ice, and the precipitate removed by a 2-min centrifugation in a Beckman microfuge. 220 µl of supernatant were applied to a Dowex 50W (200–400 mesh) cation-exchange column (0.5×2 cm), which was washed with 1 ml of distilled H2O to collect the [$^{14}$C]QUIN produced. 5.5 ml of scintillation fluid were added to the eluate and its radioactivity determined by liquid scintillation spectrometry. Preliminary experiments had indicated that 90–95% of [$^{14}$C]QUIN was collected by this procedure, whereas unreacted [$^{14}$C] 3HANA remained on the column.

Pharmaceutical Formulations

The administration in the novel method of treatment of this invention may conveniently be oral, rectal, or parenteral at a dosage level of, for example, about 1 to 3000 mg/kg, preferably about 10 to 1000 mg/kg and especially about 25 to 250 mg/kg and may be administered on a regimen of 1 to 4 hours per day. The dose will depend on the route of administration, a particularly preferred route being by intravenous infusion of an aqueous solution containing a compound according to formula I. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, syrups, powders or granules for oral administration; sterile parenteral solutions or suspensions for parenteral administration; or as suppositories for rectal administration.

To produce pharmaceutical formulations containing a compound according to the present invention in the form of dosage units for oral application, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated e.g. gum arabic, gelatine, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the above-mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the person skilled in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

We claim:

1. A compound of the general formula I

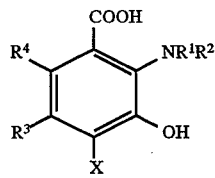

wherein $R^1$ and $R^2$ are the same or different and selected from H and alkyl;

X is selected from alkylthio, arylthio, aryloxy, halogen and cyano;

$R^3$, $R^4$ are the same or different and selected from halogen, methyl, fluoroalkyl, cyano and $Z$-$R^5$ wherein Z is selected from $CH_n$, $NH_m$, O, S, $SO_2$ and CO wherein n=1 or 2; m=0 or 1 and $R^5$ is selected from alkyl, aryl and fluoroalkyl; or $R^3$ and $R^4$ together form a saturated or unsaturated ring system Y-V-Z wherein Y and Z, independently of each other, are as defined for Z above and V is selected from $C_1$-$C_3$ alkylene or alkenylene, —N=, —N=N— and

wherein $R_7$=H or alkyl;

or a pharmaceutically acceptable salt thereof.

2. A compound according to claim 1 wherein alkyl is a straight or branched loweralkyl containing 1–6 carbon atoms, when R1, $R^2$ and/or $R^5$ represent alkyl, or when X represents alkylthio, or when $R^3$, R4 and/or $R^5$ represent fluoralkyl.

3. A compound according to claim 1 wherein X, $R^3$ and/or $R^4$ representing a halogen are selected from iodo, fluoro, chloro and bromo.

4. A compound according to claim 1 wherein aryl when $R^5$ represents aryl or when X represents an arylthio or aryloxy is a phenyl, furyl or thienyl group in which the ring is optionally further substituted by lower alkyl, lower alkoxy or halogen.

5. The compound according to claim 1 which is 4,6-dichloro-5-methylanthranilic acid.

6. A pharmaceutical formulation containing a compound according to claim 1 as active ingredient and a pharmaceutically acceptable carrier.

7. A method for the prevention or treatment of neurodegeneration which comprises administering to a host in need of such treatment a sufficient amount of a compound according to claim 1.

* * * * *